US006884219B1

(12) United States Patent
Pruter (10) Patent No.: US 6,884,219 B1
(45) Date of Patent: Apr. 26, 2005

(54) METHOD AND DISPOSABLE APPARATUS FOR GUIDING NEEDLES WITH AN ENDOCAVITY MEDICAL IMAGING DEVICE

(76) Inventor: Rick L. Pruter, 21 Woodcrest La. NE., Iowa City, IA (US) 52240

( * ) Notice: Subject to any disclaimer, the term of this patent is extended or adjusted under 35 U.S.C. 154(b) by 51 days.

(21) Appl. No.: 10/065,758

(22) Filed: Nov. 15, 2002

Related U.S. Application Data (63) Continuation-in-part of application No. 10/065,442, filed on Oct. 17, 2002, now abandoned.

(51) Int. Cl.[7] .................................................. A61B 8/14
(52) U.S. Cl. ...................................................... 600/459
(58) Field of Search ......................... 600/461, 565–567, 600/576–581; 604/110, 197, 198

(56) References Cited

U.S. PATENT DOCUMENTS

| | | | |
|---|---|---|---|
| 2,451,183 | A | 10/1948 | Tantimonaco |
| 2,536,963 | A | 1/1951 | Stephens |
| 3,017,887 | A | 1/1962 | Heyer |
| 3,538,915 | A | 11/1970 | Frampton et al. |
| 3,556,079 | A | 1/1971 | Omizo |
| 4,029,084 | A | 6/1977 | Soldner |
| 4,058,114 | A | 11/1977 | Soldner |
| 4,108,165 | A | 8/1978 | Kopp et al. |
| 4,132,496 | A | 1/1979 | Casto |
| 4,249,539 | A | 2/1981 | Vilkomerson et al. |
| 4,289,139 | A | 9/1981 | Enjoji et al. |
| 4,332,248 | A | 6/1982 | DeVitis |
| 4,363,326 | A | 12/1982 | Kopel |

(Continued)

FOREIGN PATENT DOCUMENTS

WO  WO 99/34735  7/1999

OTHER PUBLICATIONS

Solutions for Ultrasound, Civco Medical Instruments Co., Medical Parkway, 102 Highway 1 South, Kalona, IA 52247.
Disposable Transrectal Needle Guide, Civco Medical Instruments Co., Inc., Medical Parkway, 102 Highway 1 South, Kalona, IA 52247.
Maggi & Maggi II Plus, Sterile General Purpose Biopsy Needle Guides, Civco Medical Instrument Co., Inc., Medical Parkway, 102 Highway 1 South, Kalona, IA, 52247.
Aloka Needle Guide/Probe Cover Kits, Civco Medical Instruments Co., Inc., Medical Parkway, 102 Highway 1 South, Kalona, IA 52247.
Multi Pro 2000, Multi–Purpose Ultrasound Linear Tracking Instrument, Civo Medical Instruments Co., Inc., 418 B Avenue, Kalona, IA 52247.
"Endocavity Needle Guide Kits" brochure of Civco Medical Instruments, Copyright 2000, Solutions for Imaging.
"Civcoscan, Product News and Special Offers from Civco" brochure of Civco Medical Instruments, Winter 2001.
Ultra–Pro sterile General Purpose Biopsy Needle Guide, Civco Medical Instruments Co., Inc., Medical Parkway, 102 Highway 1 South, Kalona, IA 52247.
"Hitting the Mark with Realtime Guidance", Civco Program Drawer Q, Kalona, IA 52247.
Program for Medical Ultrasound Professionals,Winter 1995, Civco Medical Instrument Co., Inc., Medical Parkway, 102 Highway 1 South, Kalona, IA 52247.

(Continued)

Primary Examiner—Ali Imam
(74) Attorney, Agent, or Firm—Simmons, Perrine, Albright & Ellwoodd P.L.C.

(57) ABSTRACT

An apparatus and method for guiding a needle in conjunction with a biopsy using an endocavity medical imaging device, where a non-reusable needle guide, which is relatively inexpensive which grasps the sheathed bracket firm, and holds the same in a set position based upon a protuberance having an intentionally low shear resisting capability.

21 Claims, 5 Drawing Sheets

U.S. PATENT DOCUMENTS

| | | | |
|---|---|---|---|
| 4,402,324 A | | 9/1983 | Lindgren et al. |
| 4,408,611 A | | 10/1983 | Enjoji |
| 4,469,106 A | | 9/1984 | Harui |
| 4,489,730 A | | 12/1984 | Jingu |
| 4,491,137 A | | 1/1985 | Jingu |
| 4,497,325 A | | 2/1985 | Wedel |
| 4,504,269 A | | 3/1985 | Durand |
| 4,542,747 A | * | 9/1985 | Zurinski et al. ............ 600/461 |
| 4,567,896 A | * | 2/1986 | Barnea et al. .............. 600/443 |
| 4,635,644 A | | 1/1987 | Yagata |
| 4,742,829 A | | 5/1988 | Law et al. |
| 4,781,067 A | | 11/1988 | Cichanski |
| 4,838,506 A | * | 6/1989 | Cooper ....................... 248/200 |
| 4,883,059 A | * | 11/1989 | Stedman et al. ............ 600/437 |
| 4,898,178 A | | 2/1990 | Wedel |
| 4,899,756 A | | 2/1990 | Sonek |
| 4,911,173 A | * | 3/1990 | Terwilliger ................. 600/464 |
| 4,970,907 A | | 11/1990 | Flynn |
| 5,052,396 A | | 10/1991 | Wedel et al. |
| 5,076,279 A | | 12/1991 | Arenson et al. |
| 5,088,500 A | | 2/1992 | Wedel et al. |
| 5,161,764 A | | 11/1992 | Roney |
| 5,235,987 A | * | 8/1993 | Wolfe ......................... 600/461 |
| 5,343,865 A | | 9/1994 | Gardineer et al. |
| D362,064 S | | 9/1995 | Smick |
| 5,469,853 A | * | 11/1995 | Law et al. .................. 600/463 |
| 5,623,931 A | * | 4/1997 | Wung et al. ................ 600/461 |
| D383,968 S | | 9/1997 | Bidwell et al. |
| 5,758,650 A | * | 6/1998 | Miller et al. ................ 600/461 |
| 5,871,448 A | | 2/1999 | Ellard |
| 5,910,113 A | | 6/1999 | Pruter |
| 5,924,992 A | * | 7/1999 | Park et al. .................. 600/461 |
| 5,941,889 A | | 8/1999 | Cermak |
| D424,693 S | | 5/2000 | Pruter |
| 6,095,981 A | * | 8/2000 | McGahan .................... 600/461 |
| 6,102,867 A | * | 8/2000 | Dietz et al. ................. 600/461 |
| 6,139,544 A | | 10/2000 | Mikus |
| 6,203,499 B1 | | 3/2001 | Imling et al. |
| 6,296,614 B1 | * | 10/2001 | Pruter ......................... 600/461 |
| 6,311,084 B1 | | 10/2001 | Cormack et al. |
| 2001/0034530 A1 | | 10/2001 | Malackowski et al. |

OTHER PUBLICATIONS

"ultrasoundsupplies.com" brochure of Civco Medical Instruments Co.

"General Purpose Needle Guides and Transducer Covers" brochure of Civco Medical Insutrments, Sonosite Cross--Reference Information.

"Needle Guidance Systems, Transducer Covers, GE Medical Systems", gemedicalsystems.com brochure of Civco Medical Instruments, Solutions for Imaging.

UltraGuide 1000 System 4-page brochure, UltraGuide Ltd., Tirat Hacarmel Industrial Park, P O Box 2070, Tirat Hacarmel 30200, Israel.

UltraGuide 1000 2-page brochure, UltraGuide Ltd., Tirat Hacarmel Industrial Park, P O Box 2070, Tirat Hacarmel 30200, Israel.

"US-Guide, Free-hand Guidance for Ultrasound Interventions" brochure from UltraGuide Smart Guidance Solutions.

"Dedicated Breast Ultrasound, USI Introduces a Revolution in Breast Ultrasound . . . Vista" by USI The Breast Imaging Company.

Three-page web page of amedic.se printed on Nov. 5, 2002.

* cited by examiner

METHOD AND DISPOSABLE APPARATUS FOR GUIDING NEEDLES WITH AN ENDOCAVITY MEDICAL IMAGING DEVICE

CROSS REFERENCE TO RELATED APPLICATIONS

This is a continuation-in-part application of application Ser. No. 10/065,442 entitled "METHOD AND DISPOSABLE APPARATUS FOR GUIDING NEEDLES WITH AN ENDOCAVITY MEDICAL IMAGING DEVICE," filed on Oct. 17, 2002, now abandoned, which application relates to application entitled "METHOD AND DISPOSABLE APPARATUS FOR GUIDING NEEDLES", application Ser. No. 10/065,029, filed on Sep. 11, 2002, now U.S. Pat. No. 6,758,817, by Rick L. Pruter and Quanah Lee Bain.

BACKGROUND OF INVENTION

In recent years, handheld medical imaging transceivers, such as ultrasound and gamma ray transceivers, have been used extensively for various medical imaging situations.

In the past, the physician or medical professional typically will cover an ultrasound transceiver with a sterile sheath. Usually, under the sheath is a mounting bracket attached to the transceiver. A needle guide is then typically attached over the sheath and coupled to the underlying bracket. The sheath protects the transceiver and bracket.

While these needle guides have been used extensively in the past, they do have some drawbacks. First of all, these needle guides are not covered by the sheath and consequently, must be sterilized after each use or discarded. In the past, these needle guides have been substantial in size and in cost. The substantial nature of the needle guide can often result in the medical professional deciding to retain the needle guide and sterilize it even if the manufacturer intended it to be disposable.

Secondly, these needle guides are often at least partially inserted into a patient's rectum or vagina. When they are rotated in situ, discomfort can occur from any protuberance such as a needle guide coupled to the transceiver.

Consequently, there exists a need for improved methods and apparatus for guiding needles in an efficient manner.

SUMMARY OF INVENTION

It is an object of the present invention to provide an apparatus and method for guiding a needle in an efficient manner.

It is a feature of the present invention to include a non-reusable needle guide.

It is another feature of the present invention to include a needle guide, bracket and transceiver combination which is free from large protruding surface features which could cause patient discomfort, especially when rotated in situ.

It is another feature of the present invention to include an enlarged needle-receiving area on a needle guide to facilitate quick insertion of the needle therein.

It is another feature of the present invention to include a needle guide-to-bracket attachment mechanism which is adapted for positive attachment to the bracket with a predetermined grasping force in a non-reusable manner.

It is an advantage of the present invention to achieve improved efficiency in guiding needles.

The present invention is an apparatus and method for guiding needles, designed to satisfy the aforementioned needs, provide the previously stated objects, include the above-listed features, and achieve the already articulated advantages. The present invention is carried out in a "physician burden-less" manner in a sense that the burden on a physician or other medical professional in guiding needles during the process of insertion into the needle guide, has been greatly reduced. Additionally, the system is carried out in a reduced discomfort manner in the sense that the patient discomfort associated with rotating a transceiver/bracket/needle guide combination in situ is reduced. Finally, the present invention is carried out in a disposable manner in the sense that the base and the clamp used to couple it to the sheathed bracket are designed to be used only once and then discarded.

Accordingly, the present invention is an apparatus and method including a needle guide with enlarged needle-receiving portions on the needle guide, and base-to-bracket locks which are non-reusable.

BRIEF DESCRIPTION OF DRAWINGS

The invention may be more fully understood by reading the following description of the preferred embodiments of the invention, in conjunction with the appended drawings wherein.

DETAILED DESCRIPTION

Figure 1:
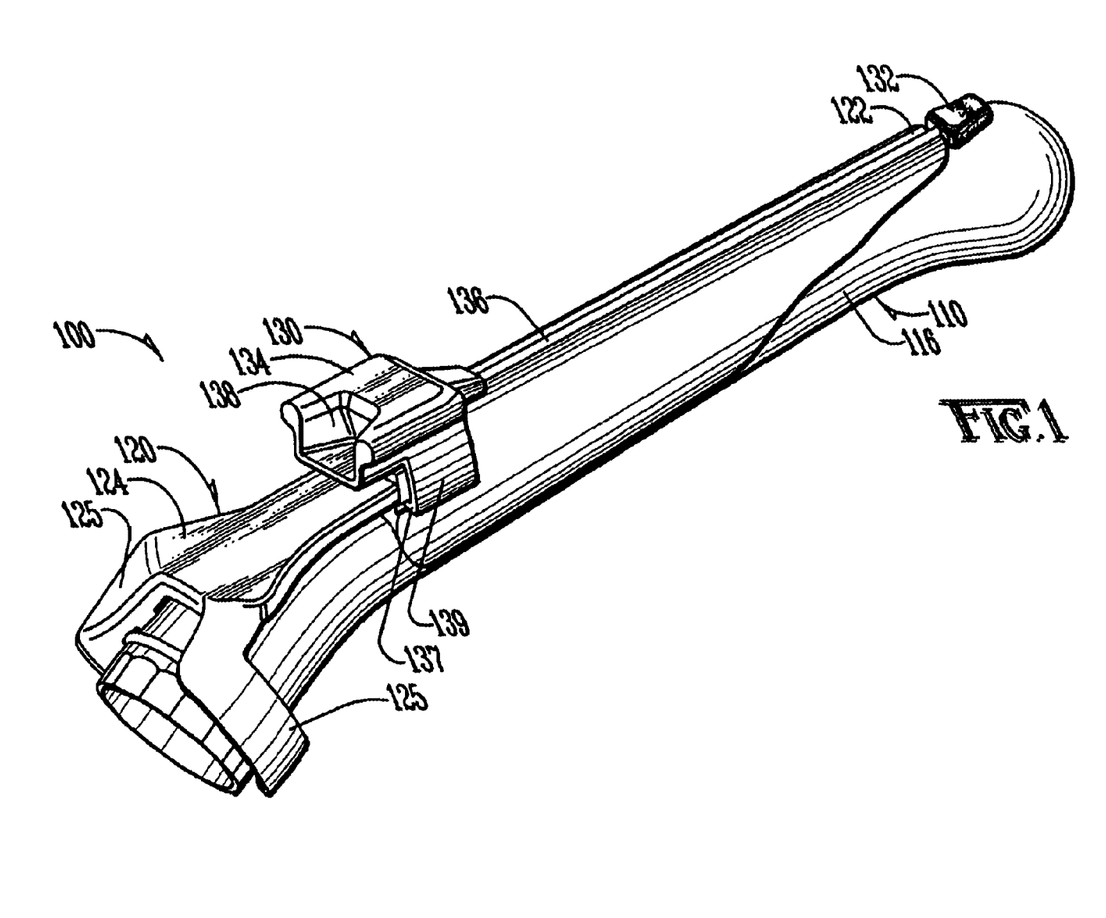
FIG. 1 is a perspective view of the apparatus of the present invention in conjunction with a medical imaging transceiver.

Now referring to the drawings wherein like numerals refer to like matter throughout, and more specifically referring to FIG. 1, there is shown a needle guide, bracket and medical imaging transceiver system of the present invention generally designated 100. The system 100 includes a medical imaging transceiver 110 which could be any type of imaging system or device, and a transceiver mounting bracket 120, which is coupled to said medical imaging transceiver 110 for the purpose of facilitating coupling with needle guides and other instruments. Medical imaging transceiver 110 is preferably an endocavity transceiver. The term "endocavity" is used herein to refer to an object, apparatus, device, etc. which is sized, shaped and configured for trans-rectal and trans-vaginal use. Mounting bracket 120 can be coupled to medical imaging transceiver 110 in any suitable manner, such as clamps, screws, adhesive, etc. Transceiver/bracket covering sterile sheath (FIG. 2) is disposed about mounting bracket 120 and medical imaging transceiver 110 in a well-known manner. Needle guide assembly 130 is shown having a needle guide enlarged proximal end 134 being enlarged with respect to side clamp leg 139.

Mounting bracket 120 is preferably designed to firmly attach to medical imaging transceiver 110 and to fill in the space available about reduced cross section medical imaging transceiver middle section 116. Mounting bracket 120 includes a mounting bracket distal end 122 and a mounting bracket proximal end 124. Mounting bracket 120 preferably is a partial sleeve which is sized and configured to be placed over the reduced cross-section medical imaging transceiver middle section 116 and to firmly grasp medical imaging transceiver 110. Mounting bracket 120 may have at its mounting bracket proximal end 124 a plurality of bracket clamp legs 125. Now referring to FIG. 2, the mounting bracket 120 includes a mounting bracket needle guide receiving slot 226 and a mounting bracket needle guide receiving platform 228, as well as a mounting bracket protuberance receiving void 227.

Figure 2:
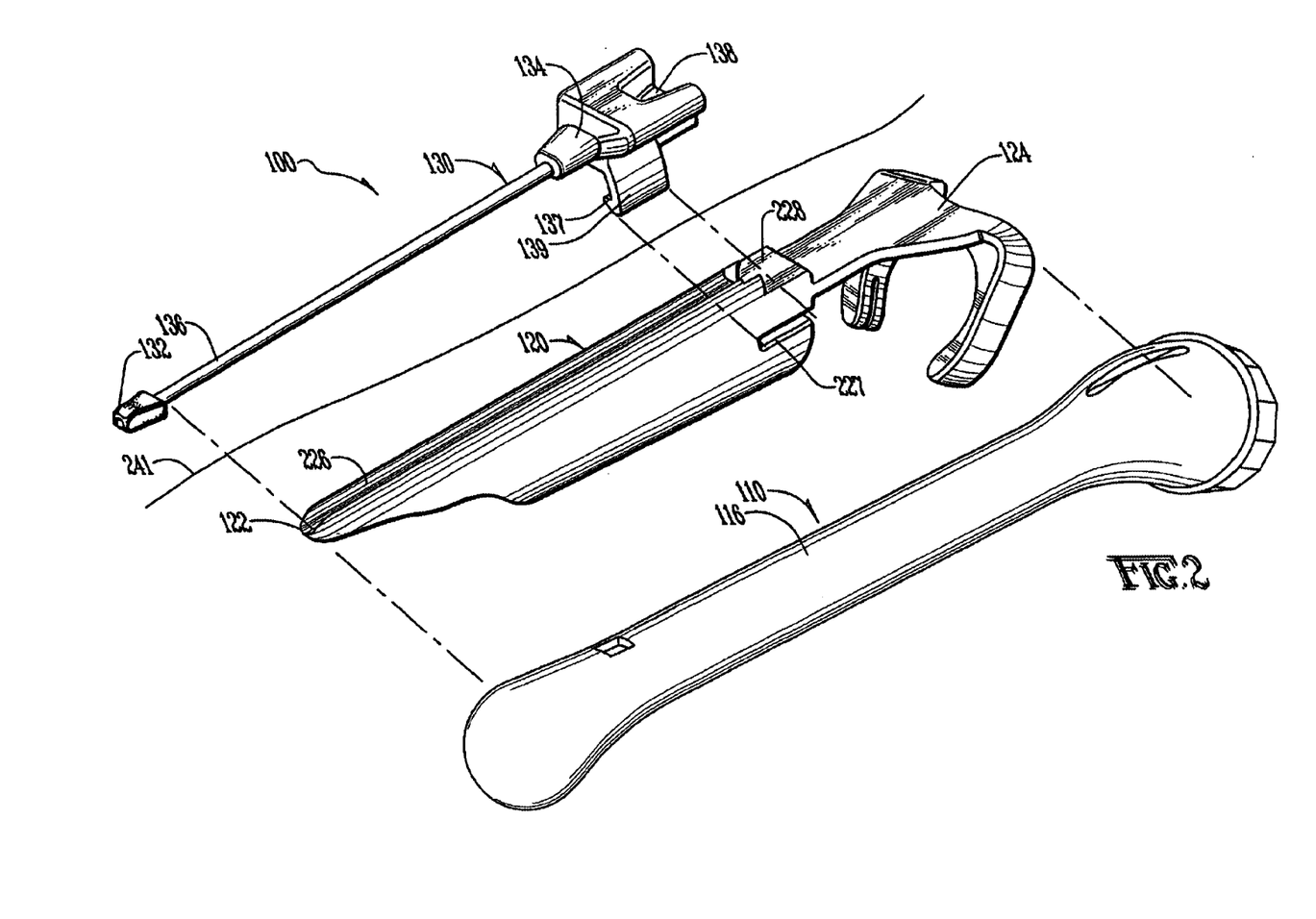
FIG. 2 is an exploded perspective diagram of the apparatus of FIG. 1 where the dashed lines represent lines along which the respective elements have been moved. Portions of sterilized sheath 241 are represented in a cross-sectional view.
Figure 3:
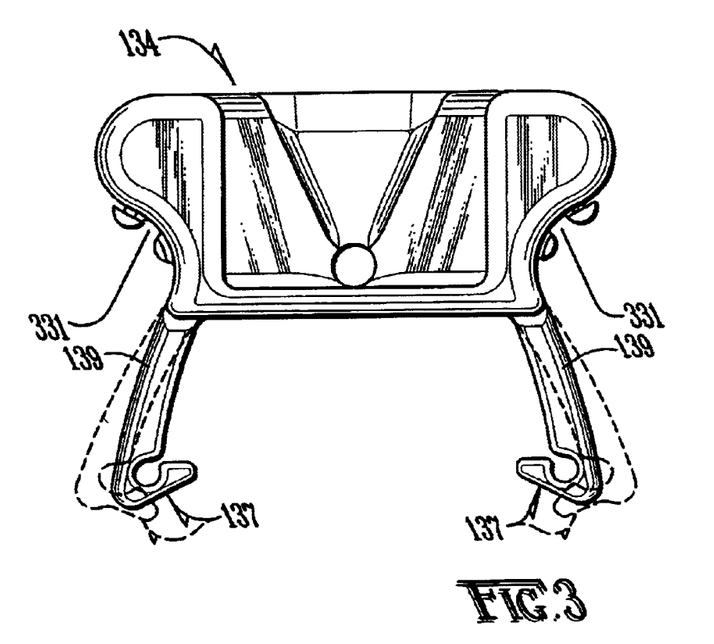
FIG. 3 is an end view of the proximal end 134 of the needle guide 130.

Now Referring to FIGS. 1, 2 and 3, there is shown a needle guide 130 of the present invention. Needle guide 130 includes a needle guide distal end 132 and a needle guide enlarged proximal end 134 and a needle guide central cannula section 136. Needle guide enlarged proximal end 134 is preferably larger than side clamp leg 139 and thereby creating a needle guide grasping depression 331, (FIG. 3) into which a person finger can rest when a force is applied to the needle guide 130 to separate it from the sheath covered mounting bracket 120. Preferably, the orientation of side clamp leg protuberance 137, side clamp leg 139 and mounting bracket protuberance receiving void 227 are such that when a lifting force is applied on needle guide enlarged proximal end 134, the side clamp leg protuberance 137 is caused to shear off before side clamp leg 139 is spread sufficiently to allow non-destructive removal of the needle guide 130 from the sheathed mounting bracket 120. Numerous other methods of securing needle guide 130 to mounting bracket 120 exist which would necessitate destruction upon removal. For example, needle guide 130 might include a bullet-nose plastic member which locks upon insertion and is only unlocked by destruction of the bullet-nose member. Still other well-known means of attachments could be used as well.

In operation, the apparatus and method of the present invention as described and shown in FIGS. 1–3, could function as follows:

Mounting bracket 120 is mounted on a medical imaging transceiver 110. A transceiver/mounting bracket sterile sheath 241 is pulled over the medical imaging transceiver 110 and mounting bracket 120 combination. Needle guide 130 is pushed onto mounting bracket 120, so that side clamp leg 139 separates (see dotted lines in FIG. 3) to allow further depression until side clamp leg protuberance 137 slips into mounting bracket protuberance receiving void 227, thereby firmly attaching needle guide 130 to the transceiver/mounting bracket sterile sheath 241 covered mounting bracket 120. Needle guide central cannula section 136 fits into mounting bracket needle guide receiving slot 226. When needle guide 130 is firmly attached to mounting bracket 120, the medical professional can insert a needle or other instrument into needle guide enlarged needle receiving area 138 and then into the needle guide central cannula section 136. Ultimately, the needle or other instrument is disposed beyond the mounting bracket distal end 122 and is able to enter a patient's tissue.

Figure 4:
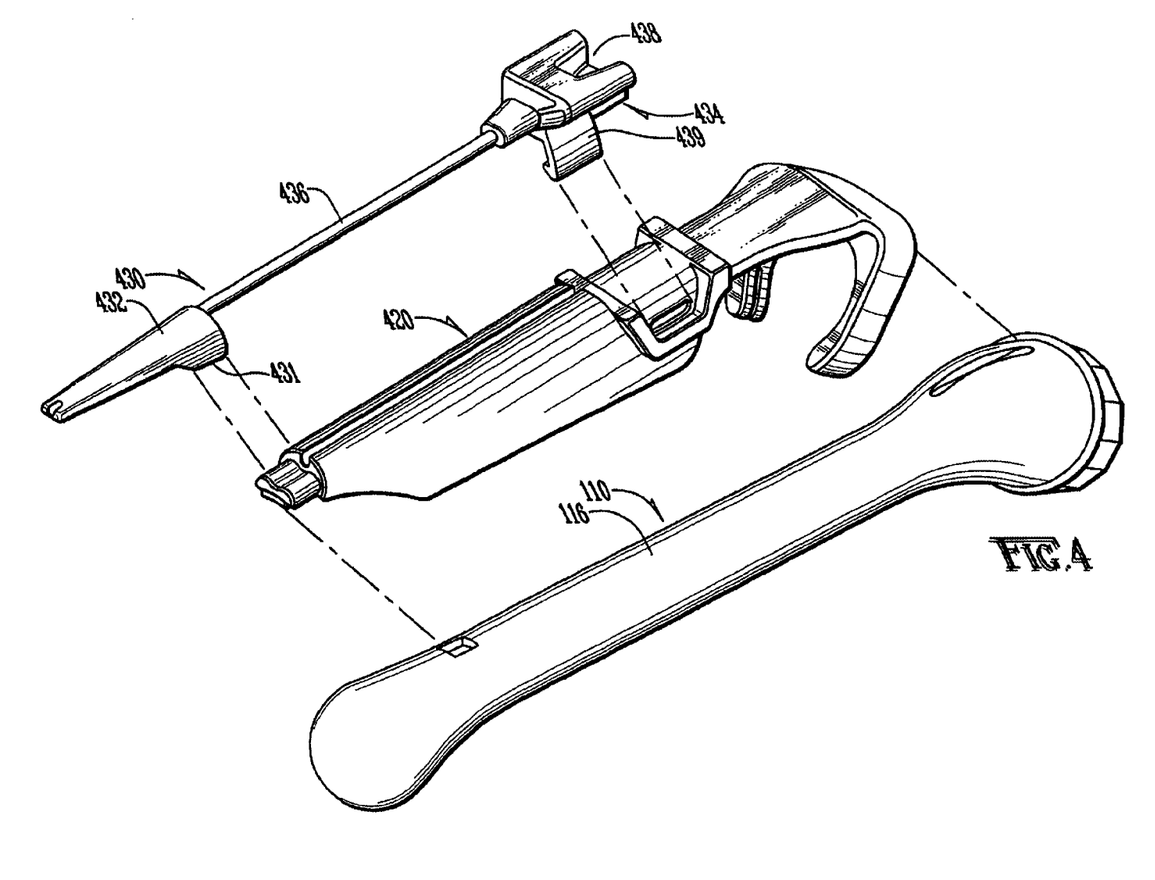
FIG. 4 is an exploded diagram of an alternate embodiment of the present invention which shows a front clip.
Figure 5:
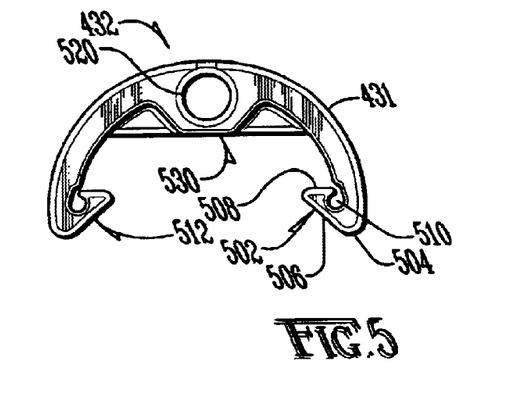
FIG. 5 is a cross-sectional view of the front clip of FIG. 4.

Now referring to FIGS. 4 and 5, there is shown an alternate embodiment of the present invention, which includes a medical imaging transceiver 110 and a dual clip needle guide mounting bracket 420 and a dual clip needle guide 430. Dual clip needle guide mounting bracket 420 is similar to mounting bracket 120 except for the variations required to mate with the dual clip needle guide 430 instead of the needle guide 130. Dual clip needle guide mounting bracket 420 couples to medical imaging transceiver 110 as described above with respect to mounting bracket 120. Dual clip needle guide 430 includes a dual clip needle guide front clip end 432 and a dual clip needle guide needle inlet end 434. Dual clip needle guide needle inlet end 434 includes a dual clip needle guide funnel 438 and a dual clip needle guide bracket leg 439. Dual clip needle guide 430 also includes a dual clip needle guide front clip end 432 which is separated by the cannula 436. Dual clip needle guide front clip end 432 includes a front leg 431, which has a dual clip needle guide leg protuberance 502 disposed along its inside distal end. Dual clip needle guide leg protuberance 502 includes a dual clip needle guide leg protuberance leading edge 504, a dual clip needle guide leg protuberance insertion contact surface 506, a dual clip needle guide leg protuberance seated contact surface 508 and a dual clip needle guide leg protuberance to leg void 510.

Dual clip needle guide front clip end 432 also includes a second dual clip needle guide leg protuberance 512, a dual clip needle guide front cannula section 520 and a dual clip needle guide front flat base section 530.

Figure 6:
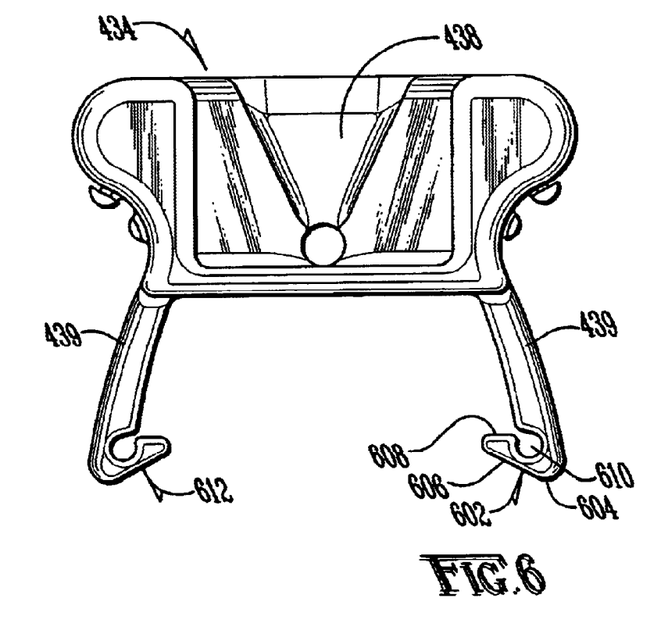
FIG. 6 is a cross-sectional view of the rear clip of FIG. 4.

Now referring to FIG. 6, there is shown a cross-sectional view of dual clip needle guide needle inlet end 434, which includes a dual clip needle guide rear clip leg protuberance 602, dual clip needle guide rear leg protuberance leading edge 604, dual clip needle guide rear leg protuberance insertion contact surface 606, dual clip needle guide rear leg protuberance seated contact surface 608 and dual clip needle guide rear leg protuberance to leg void 610 and a second dual clip needle guide rear leg protuberance 612.

The alternate embodiment of FIGS. 4–6 operates as follows:

The dual clip needle guide 430 is pressed down onto dual clip needle guide mounting bracket 420. Dual clip needle guide leg protuberance insertion contact surface 506 and dual clip needle guide rear leg protuberance insertion contact surface 606 contact the exterior of dual clip needle guide mounting bracket 420. Dual clip needle guide bracket leg 439 and front leg 431 spread apart as dual clip needle guide 430 is pressed harder downward. When dual clip needle guide leg protuberance 502 and dual clip needle guide rear clip leg protuberance 602 reach voids in the side of dual clip needle guide mounting bracket 420, they are forced into such voids. When dual clip needle guide leg protuberance 502 and dual clip needle guide rear clip leg protuberance 602 are in the voids, they firmly hold the dual clip needle guide 430 to the dual clip needle guide mounting bracket 420.

When the dual clip needle guide 430 is to be removed, upward pressure is applied to the dual clip needle guide needle inlet end 434 and dual clip needle guide front clip end 432. Because of the reduced thickness associated with dual clip needle guide leg protuberance to leg void 510 and dual clip needle guide rear leg protuberance to leg void 610, the dual clip needle guide leg protuberance 502 and the dual clip needle guide rear clip leg protuberance 602 respectively, are deformed beyond their elastic limits, and dual clip needle guide 430 becomes removable from the voids in dual clip needle guide mounting bracket 420. Once dual clip needle guide leg protuberance 502 and dual clip needle guide rear clip leg protuberance 602 are deformed beyond their elastic limits, they are no longer capable of causing the dual clip needle guide 430 to be firmly attached to dual clip needle guide mounting bracket 420.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well, where it is desirable to guide a needle or other elongated medical instrument.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

What is claimed is:

1. A medical imaging system comprising:
    a transceiver bracket being sized, shaped and configured for securing with an endocavity medical imaging transceiver;
    a transceiver/bracket covering sterile sheath disposed over said medical imaging transceiver and said transceiver bracket;
    a needle guide disposed over said transceiver/bracket covering sterile sheath and cooperating with said transceiver bracket;
    a lock comprising a void in said transceiver bracket and a first pliable side clamp leg with a first side clamp leg protuberance formed thereon;
    said needle guide being attached to said transceiver bracket by said lock; and
    said first side clamp leg protuberance being configured to separate from said first side clamp leg at a level of applied force which is lower than a level of applied force which would case said needle guide to be detached from said transceiver bracket.

2. A system of claim 1 wherein said first side clamp leg is coupled to a needle guide.

3. A system of claim 2 further comprising a second side clamp leg disposed on an opposing side of said needle guide.

4. A system of claim 3 further comprising a second side clamp leg protuberance coupled to said second side clamp leg and disposed on an opposing side of said needle guide with respect to said first side clamp leg protuberance.

5. A system of claim 1 wherein said needle guide further comprises a needle guide enlarged needle-receiving area which is sized and configured to receive needles at locations and angles which would otherwise exclude mating of a needle with a needle guide central cannula section.

6. A system of claim 5 further comprising a needle guide having a needle guide enlarged proximal end which facilitates gasping of said needle guide and pulling in a predetermined direction.

7. An endocavity medical imaging system comprising:
    an endocavity medical imaging transceiver, for generating image signals;
    a mounting bracket, coupled to said endocavity medical imaging transceiver;
    a needle guide sized and configured to couple with said mounting bracket so as to create a lock between said needle guide and said mounting bracket when a protuberance mates with a structure; and,
    said lock being a single use lock such that once said protuberance is removed from said structure, said lock is theater incapable of affixing said needle guide to said mounting bracket.

8. A system of claim 7 wherein said lock comprises a plurality of protuberances.

9. A system of claim 8 wherein said structure is a void in said mounting bracket.

10. A system of claim 9 having a needle guide central cannula section which is recessed in a mounting bracket needle guide receiving slot in said mounting bracket.

11. A system of claim 10 wherein said mounting bracket is a partial sleeve disposed about a reduced cross-section medical imaging transceiver middle section of said endocavity medical imaging transceiver.

12. A system of claim 11 wherein said partial sleeve is sized and configured to provide a clamping force on said reduced cross-section medical imaging transceiver middle section so as to secure said partial sleeve to said reduced cross-section medical imaging transceiver middle section.

13. A system of claim 12 wherein said needle guide is sized and configured to apply a needle guide clamping force on said mounting bracket by biasing each of a plurality of protuberances into contact with a structure.

14. A system of claim 13 wherein said needle guide clamping force is created when said needle guide is moved toward said mounting bracket along a line substantially perpendicular to a longitudinal axis of said mounting bracket.

15. A system of claim 14 wherein said each of said plurality of protuberances has a strength characters of attachment to said needle guide such that said strength characteristic of attachment to said needle guide is sufficient to allow each of said plurality of protuberance to maintain in a full contact relationship with said needle guide when said needle guide is moved along said line toward said mounting bracket and said strength characteristic of attachment to said needle guide is insufficient to maintain said full contact relationship for all of said plurality of protuberances, when said needle guide is moved along said line in a direction away from said mounting bracket, so that said needle guide becomes detached from said mounting bracket.

16. A system of claim 15 wherein one of said plurality of protuberances is sheared from said full contact relationship when said needle guide is moved along said line away from contact with said mounting bracket.

17. An apparatus for guiding a medical instrument in proximity to an endocavity medical imaging transceiver, the system comprising:
    a medical instrument central cannula section, having a cannula longitudinal axis with a hole running along said cannula longitudinal axis, said hole being sized and configured to receive therethrough a medical instrument which is capable of translational motion along said cannula longitudinal axis;
    means for locking said medical inset central cannula section to an exterior surface, such that said medical instrument central cannula section is no longer capable of locking to said exterior surface, after said medical instrument central cannula section is once locked to said exterior surface and then removed from said exterior surface; and
    where said exterior surface is an exterior surface of an endocavity member having an endocavity longitudinal axis which is parallel to said cannula longitudinal axis.

18. An apparatus of claim 17 wherein said means for locking comprises a protuberance which mates with a void to lock and said protuberance becomes at least partially detached when said medical instrument central cannula section is removed from said exterior surface.

19. A method of guiding medical instruments in conjunction with an endocavity medical imaging transceiver comprising the steps of:
    providing an endocavity transceiver, for generating image signals representative of internal portions of a human body;
    securing a cannula to said endocavity transceiver;

inserting said endocavity transceiver and said cannula into an orifice of a human body;

providing a medical instrument;

manipulating said medical instrument within said cannula;

removing said endocavity receiver from said orifice;

pulling said cannula away from said endocavity transceiver such that means coupled to said cannula for securing to said endocavity transceiver is no longer capable of securing said cannula to said endocavity transceiver; and, disposing said cannula.

20. A system for guiding needles comprising:

an endocavity medical imaging transceiver configured for generating image signals representative of interior portions of a human body;

a mounting bracket coupled to said endocavity medical imaging transceiver;

a needle guide coupled to said mounting bracket;

said mounting bracket having a partial sleeve shape configured for coupling with a reduced cross-section medical imaging transceiver middle section of said endocavity medical imaging transceiver;

said mounting bracket further having a mounting bracket distal end and a mounting bracket proximal end and a mounting bracket needle guide receiving slot disposed between said mounting bracket distal end and said mounting bracket proximal end;

said mounting bracket further having a mounting bracket protuberance receiving void there;

said needle guide comprising a needle guide distal end and a needle guide enlarged proximal end and a needle guide central cannula section disposed therebetween;

said needle guide further comprises a side clamp leg with a side clamp leg protuberance thereon, where the side clamp leg protuberance is separated from the side clamp leg by a substantially circular-shaped void;

said needle guide further including a needle guide enlarged needle-receiving area having a funnel region for guiding needles into said needle guide central cannula section;

said side clamp leg protuberance is configured to mate with mounting bracket protuberance receiving void and to secure said needle guide to said mounting bracket;

said side clamp leg protuberance having a predetermined strength characteristic which is insufficient to keep said side clamp leg protuberance intact with said side clamp leg when said needle guide is removed from said mounting bracket by applying a lifting force on said needle guide in a direction substantially perpendicular to a longitudinal axis of said needle guide central cannula section.

21. A method of guiding a needle with to a medical imaging transceiver, comprising the steps of:

providing an endocavity medical imaging transceiver and a transceiver bracket disposed in a transceiver/bracket covering sterile sheath;

providing a needle guide outwardly of said sheath;

engaging a lock member which fixes said needle guide to said transceiver bracket;

positioning said endocavity medical imaging transceiver within a body cavity;

inserting a needle into said needle guide;

performing a medical procedure using said needle and said medical imaging transceiver;

removing said needle from said needle guide;

applying a force on said lock member which permanently damages said lock member; and, discarding said needle guide.

* * * * *

UNITED STATES PATENT AND TRADEMARK OFFICE
CERTIFICATE OF CORRECTION

PATENT NO. : 6,884,219 B1
DATED : April 26, 2005
INVENTOR(S) : Rick L. Pruter

It is certified that error appears in the above-identified patent and that said Letters Patent is hereby corrected as shown below:

Column 5,
Line 62, please delete the word "theater" and insert therefor -- thereafter --.

Column 6,
Line 23, please delete the word "characters" and insert therefor -- characteristic --.
Line 55, please delete the word "where" and insert therefor -- wherein --.

Column 7,
Line 6, please delete the word "receiver" and insert therefor -- transceiver --.
Line 30, please delete the word "there" and insert therefor -- therein --.

Column 8,
Line 18, after the word "with", please insert the word -- respect --.

Signed and Sealed this

Thirtieth Day of August, 2005

JON W. DUDAS
*Director of the United States Patent and Trademark Office*